United States Patent
Sun (10) Patent No.: US 11,324,632 B2
(45) Date of Patent: May 10, 2022

(54) HELMET WITH INWARDS FLIPPING TYPE GOGGLE

(71) Applicant: ANHUI HENGYU OPTICAL ELECTRONICS CO., LTD, Hefei (CN)

(72) Inventor: Haijian Sun, Hefei (CN)

(73) Assignee: ANHUI HENGYU OPTICAL ELECTRONICS CO., LTD, Hefei (CN)

( * ) Notice: Subject to any disclaimer, the term of this patent is extended or adjusted under 35 U.S.C. 154(b) by 384 days.

(21) Appl. No.: 16/479,607

(22) PCT Filed: Mar. 13, 2019

(86) PCT No.: PCT/CN2019/077941
§ 371 (c)(1),
(2) Date: Jul. 22, 2019

(87) PCT Pub. No.: WO2020/151062
PCT Pub. Date: Jul. 30, 2020

(65) Prior Publication Data
US 2021/0330505 A1    Oct. 28, 2021

(30) Foreign Application Priority Data

Jan. 24, 2019  (CN) .......................... 201910068658.9

(51) Int. Cl.
*A61F 9/06*   (2006.01)
*A61F 9/02*   (2006.01)
*F16P 1/06*   (2006.01)

(52) U.S. Cl.
CPC .............. *A61F 9/061* (2013.01); *A61F 9/029* (2013.01); *F16P 1/06* (2013.01)

(58) Field of Classification Search
CPC .. A61F 9/06; A61F 9/061; A61F 9/064; A61F 9/029; A42B 3/18; A42B 3/185;
(Continued)

(56) References Cited

U.S. PATENT DOCUMENTS 2,036,224 A  *  4/1936  Lincoln ................... A61F 9/061
                                                      219/147
3,086,212 A  *  4/1963  Hill .......................... A61F 9/061
                                                      2/8.3
(Continued)

FOREIGN PATENT DOCUMENTS

CN          2507431 Y       8/2002
CN         104258638 A      1/2015
(Continued)

*Primary Examiner* — F Griffin Hall
(74) *Attorney, Agent, or Firm* — Zhihua Han; Wen IP LLC (57) ABSTRACT

The present invention discloses a helmet with an inwards flipping type goggle, which includes a helmet body, a goggle, a front protection lens and a link mechanism; the front protection lens is fixed to the front side of the helmet body, the goggle is fixed to the link mechanism, the link mechanism is capable of adjusting the goggle to move up and down and to be rotatably connected to the two sides of the helmet body, and the goggle are located in the helmet body. The present invention has the following beneficial effects: by adopting the inwards flipping type, the goggle are prevented from being easily contaminated by welding splash, grinding splash and dust when the goggle are upwards flipped outside; the defects that the gravity center of the entire helmet moves forwards and the helmet is heavy are avoided; the goggle can be upwards flipped inside the helmet, the sight is not affected under the situation that the helmet is not taken off, and it is applicable to wider occasions, is more flexible and is more convenient to operate.

4 Claims, 9 Drawing Sheets

(58) Field of Classification Search
CPC ........... A42B 3/22; A42B 3/221; A42B 3/222; A42B 3/223; A42B 3/225; A42B 3/228; F16P 1/06
USPC ......................................... 2/8.3, 8.4, 8.5, 8.6
See application file for complete search history.

(56) References Cited

U.S. PATENT DOCUMENTS

| | | | | |
|---|---|---|---|---|
| 4,993,617 | A * | 2/1991 | Yang | A61F 9/061 |
| | | | | 2/11 |
| 8,826,464 | B2 * | 9/2014 | Wu | A61F 9/061 |
| | | | | 2/8.2 |
| 9,610,198 | B2 * | 4/2017 | Hofer-Kraner | A61F 9/067 |
| 2004/0210976 | A1 * | 10/2004 | Huh | A61F 9/067 |
| | | | | 2/8.6 |
| 2018/0280197 | A1 * | 10/2018 | Patel | A61F 9/067 |

FOREIGN PATENT DOCUMENTS

| | | |
|---|---|---|
| CN | 108497604 A | 9/2018 |
| CN | 109248023 A | 1/2019 |
| KR | 1020030066240 B1 | 3/2005 |

* cited by examiner

HELMET WITH INWARDS FLIPPING TYPE GOGGLE

CROSS REFERENCE TO RELATED APPLICATION

This application is a national stage application of International application number PCT/CN2019/077941, filed Mar. 13, 2019, titled "HELMET WITH INWARDS FLIPPING TYPE GOGGLE," which claims the priority benefit of Chinese Patent Application No. 201910068658.9, filed on Jan. 24, 2019, which is hereby incorporated by reference in its entirety.

TECHNICAL FIELD

The present invention relates to a welding protection helmet, in particular to a helmet with an inwards flipping type goggle.

BACKGROUND

With the progress of the society, people have higher requirements on personal protection and improvement of production efficiency. In many occasions, hand-held welding protection helmets are used, such as application No. 201720792053.0 has disclosed a welding protection helmet, including a protection helmet, the lower portion of the protection helmet being connected to a handle, and an observation window on which a light filter lens (equivalent to the goggle in the present application document) is mounted being arranged on the panel of the protection helmet, wherein the welding protection helmet further includes an inner heat insulating helmet. This hand-held helmet must be held by a hand and it is inconvenient to operate.

Moreover, the welding protection helmets that emerge later, ranging from simple protection helmets made of dark glass and red steel paper to various automatic light filtering type protection helmets (equivalent to the automatic light filtering type variable-color-number goggle in the present application document), still cannot satisfy the requirements of people on the function and comfort. For example, before putting on the welding helmet for welding, it is required that an operator can clearly observe the workpiece and the surrounding environment, and after welding, the operator can clearly see the environment and the workpiece during slag cleaning and grinding of the welding seam. Although the automatic light filtering type protection helmet can solve some problems, its transmittance is only 8% under the situation that it does not become black. In many cases, it cannot meet the requirement of the operator on clearly seeing the workpiece and the surrounding environment.

Therefore, people invented flip helmets. For the existing flip helmets, the goggle together with the outer protection lens in front of the goggle is simply flipped forwards and upwards. However, this kind of helmets has many drawbacks which are not popular with the operators. For example, the goggle must be designed as much as possible in front of the helmet at a position far away from the eyes. Otherwise, the goggle cannot be flipped, leading to sight narrowing in the case of the window with the same size. The gravity center of the helmet moves forwards, which results in worse stress. Especially after the goggle is flipped, the center of the helmet moves forwards and upwards, and the head and the neck will be subjected to double lever force. At the same time, when the goggle is flipped, the operation is affected, the outer protection lens is also flipped along with the goggle, so it is required to design a transparent sealed protection goggle lens with the same protection requirements as the front protection lens inside the helmet. In particular, when the goggle is an automatic variable-color-number large-window goggle, the above drawbacks will be more serious because the automatic variable-color-number goggle is heavier, the entire outwards flipping portion will be heavier, and the overall weight of the helmet will be greatly increased. Therefore, the use and promotion of these products are greatly affected.

For example, application No. 201710845243.9 has disclosed a welder protection helmet, including a helmet, the upper portion of the helmet being provided with a goggle box, wherein a lower lens (equivalent to the inner protection lens in the present application) are fixed at the lower portion of the goggle box, the upper portion of the goggle box is hinged to the lower portion, can be rotated by 120 degrees, an upper lens (equivalent to the goggle in the present application) are fixed at the upper portion of the goggle box, the lower lens is a transparent lens, the upper lens is a black lens, the rear portion of the helmet is provided with a fixing rope, the fixing rope is an elastic rope, which can be rotated by 180 degrees at the position connected to the helmet. The goggle box can be upwards flipped. Therefore, for the purpose of protection, the lower lens should be designed. After the goggle box is flipped, the gravity center of the helmet moves forwards, and the field of view of the lower lens is small and it is inconvenient to operate.

In conclusion, the existing technologies include common head-mounted flip welding helmets and automatic light filtering type flip welding helmets, which have the common shortcomings that the goggle and the outer protection lens are flipped outwards at the same time, and the outer structure of the helmet is affected because a layer of transparent protection lens needs to be designed inside if the outer protection lens is flipped; because of the outwards flipping function of the goggle, especially when the goggle is flipped, the gravity center of the helmet will move forwards and upwards, which adds an additional lever force to the head and neck of the operator and causes the gravity center unstable; the goggle moves forwards and the sight becomes relatively narrower; when the goggle is flipped outwards, the goggle is easily contaminated by welding slag splash, and grinding splash and dust; and the overall weight of the helmet increases, which cause too many side effects to users.

It needs be noted that the goggle mentioned above may be either a filter lens with a fixed color number (i.e., fixed transmittance) or an automatic dimming type filter lens.

Especially, at present, with the improvement of people's self-protection consciousness, many operators require that fresh air supply systems and sealing covers be additionally mounted on the helmets. Since the environment air is polluted during welding, even if the welding is stopped, the operator should not take off the helmets with air supply systems. Otherwise, the polluted air will be inhaled. This requires that the window of the helmet must be highly transparent and have a large field of view. Otherwise, it will cause inconvenience to the work, and even bring potential safety hazards.

The information disclosed in the related art is intended only to increase the understanding of the overall background of the present invention, and should not be regarded as acknowledging or implying in any form that the information constitutes the prior art known to a person of ordinary skill in the art.

SUMMARY

The technical problem to be solved by the present invention is to provide a helmet with an inwards flipping type goggle which can overcome the disadvantages such as that the gravity center of the outwards flipping type helmet in the related art is instable, the helmet is heavy, the sight is not good, and the goggle is easily damaged and contaminated.

The present invention solves the above technical problem through the following technical solution: the present invention discloses a helmet with an inwards flipping type goggle, which includes a helmet body, a goggle, a front protection lens and a link mechanism; the front protection lens is fixed to the front side of the helmet body, the goggle is fixed to the link mechanism, the link mechanism is capable of adjusting the goggle to move up and down and to be rotatably connected to the two sides of the helmet body, and the goggle is located in the helmet body. By adopting the inwards flipping manner, the goggle in the present invention is prevented from the problems of being easily contaminated by welding splash, grinding splash and dust of the outwards flipping goggle, and prevented from the defects that the gravity center of the entire helmet moves forwards and the helmet is heavy of the outwards flipping goggle; the goggle can be inwards flipped, it is applicable to occasions in which the helmet cannot be taken off, the applicable occasions are wider and the flexibility is higher; the front protection lens can be large and wide enough, and the sight is good; and the structure is simple such that the entire helmet is more simple, concise and light.

Preferably, the link mechanism includes a link rack and a rocker arm link, one end of the rocker arm link is rotatably connected to the side surface of the helmet body through a first connecting shaft, the other end of the rocker arm link is fixedly connected to the middle portion of the link rack through a second connecting shaft, the link rack is placed in the helmet body, one end of the link rack is fixedly connected to the goggle, the other end is slidably connected to the helmet body through a third connecting shaft, and the first connecting shaft, the second connecting shaft and the third connecting shaft are sequentially far away from the front side of the helmet body. In the present invention, the link rack is driven to move up and down and rotate through the rotation of the rocker arm link, such that the gravity center of the helmet body does not move forwards and is prevented from causing pressure to the neck; since the first connecting shaft, the second connecting shaft and the third connecting shaft are sequentially far away from the front side of the helmet body, it is ensured that, when the second connecting shaft rotates around the fixed first connecting shaft, the motion vector direction of the link rack is forward and upward.

Preferably, the front end of the link rack is of a vertical structure and is provided with a plurality of connecting holes for connecting with the goggle, and the goggle is connected to the link rack through the connecting holes; and the tail end of the link rack is provided with a horizontal sliding groove, and the third connecting shaft penetrates through the sliding groove and is fixed to the helmet body, and the middle portion of the link rack is provided with a circular hole connected to the rocker arm link. According to the present invention, detachable connection is realized through the goggle and the connecting holes, and replacement and mounting are facilitated; the arrangement of the sliding groove ensures that the goggle can reach the determined position space when moving up and down and rotating, the free movement of the link rack is restricted, and the controllable movement of the goggle on the specified trajectory is ensured.

Preferably, the helmet with an inwards flipping type goggle further includes a sector-shaped limiting plate, the limiting plate is fixed to the helmet body and covers the external portion of the rocker arm link, and one end, far from the first connecting shaft, of the limiting plate is provided with a sector-shaped groove; one side, facing to the internal portion of the helmet body, of the limiting plate is provided with a first hollow cylinder, the first cylinder is arranged at the small end of the limiting plate, one end of the rocker arm link is provided with a sleeve, the sleeve rotatably sleeves the first hollow cylinder, and the first connecting shaft is in fit connection with the first hollow cylinder. The arrangement of the limiting plate can realize the carrier for the fixation of the rocker arm link, which does not need to be fully and directly mounted on the helmet body, thus realizing the movable connection between the rocker arm link and the helmet body, and realizing the degree of freedom of rotation of the rocker arm link and the simplification of the production process. Since the limiting plate covers the outer side of the rocker arm link, the rocker arm link can be protected to a certain extent, and the limiting plate and the helmet body are hermetically connected as much as possible.

Preferably, the helmet with an inwards flipping type goggle further includes a return spring, the return spring sleeves the outside of the sleeve, the two ends of the return spring are bent, the bottom end is inserted into the rocker arm link and the top end is fixed to the limiting plate. The arrangement of the return spring makes it more easy to rotate the rocker arm link downwards, the goggle can be tightly pressed onto the window of the helmet body through part of the elastic force, and the sealing performance is improved.

Preferably, one end, connected to the link rack, of the rocker arm link is provided with a handle, the handle is arranged on one side, back on to the helmet body, of the rocker arm link, penetrates through the sector-shaped groove and extends to the outside of the limiting plate, the top end of the handle is provided with a fastener, the fastener is of a concave structure, one end, far away from the first connecting shaft, of the limiting plate is provided with at least two clamping grooves, one end of the fastener is clamped in the clamping groove, the other end is clamped outside the clamping groove, one end, facing to the internal portion of the helmet body, of the rocker arm link is provided with a second hollow cylinder, and the second connecting shaft is in fit connection with the second hollow cylinder.

According to the present invention, the fitting between the fastener and the clamping groove ensures that the goggle can move in at least two positions and can be positioned at any position to ensure the stability in use, especially when the goggle is on the front side of the forehead; the fixed connection between the second connecting shaft and the second hollow cylinder realizes the fixed connection between the middle portion of the link rack and the rocker arm link.

Preferably, the helmet body is of a semi-enclosed structure, the front side of the helmet body is provided with an opening for mounting the front protection lens and a window fit with the goggle, the two sides are provided with sector-shaped holes corresponding to the limiting plate, and the limiting plate is fixedly connected at the sector-shaped holes.

Preferably, the helmet with an inwards flipping type goggle further includes an air supply system, the air supply system includes an air supply pipe and an air supply port, and the air supply port is formed in the inner side surface of the top portion of the helmet body, and the air supply pipe is connected to the air supply port. The arrangement of the air supply system can provide fresh air to the internal portion of the comparatively or completely sealed helmet.

Preferably, the air supply port is of a divergent structure and the air supply port includes a plurality of sub-air supply ports. The air supply port is divergent such that the air can be distributed more divergently and uniformly.

Preferably, the two sides of the goggle are further provided with solar power supply panels, such that solar power can be obtained, and it is more convenient to use and is more environment-friendly.

Preferably, the goggle is a fixed-color-number goggle or an automatic light filtering type variable-color-number goggle or a magnifier.

Compared with the prior at, the present invention has the following advantages:

(1) The present invention adopts the inwards flipping type goggle, such that the goggle can move up and down and rotate through link mechanism in the narrow space in the helmet and at the head and face of the wearer, and is prevented from the problem of being contaminated by welding splash, polishing splash and dust of the outwards flipping goggle; the defects that the gravity center of the entire helmet moves forwards and the helmet is heavy are avoided; the goggle can move up and down and rotate, it is applicable to occasions in which the helmet cannot be taken off, the applicable occasions are wider and the flexibility is higher; after the goggle is inwards flipped, the workpiece and the environment can directly observed through the wide, large and transparent front protection lens, such that the sight is clear and wide; the structure is simple such that the entire helmet is more simple, concise, light and applicable; it is not needed to provide two layers of transparent front protection lenses at the same time and only one layer of front protection lens is needed.

(2) By rotating the rocker arm link, the link rack moves forwards and upwards, such that the gravity center of the helmet body does not move forwards, the pressure is prevented from being applied to the neck, and the link mechanism has a simple structure and is convenient to operate; according to the present invention, detachable connection is realized through the goggle and the connecting holes, and replacement and mounting are facilitated; the arrangement of the sliding groove ensures that the goggle can reach the determined position space when moving up and down and rotating, the free movement of the link rack is restricted, and the controllable movement of the goggle on the specified trajectory is ensured; the arrangement of the limiting plate can realize the movable connection between the rocker arm link and the helmet body, can maintain the degree of freedom of rotation of the rocker arm link and can realize the simplification of the production process, and the rocker arm link can be protected to a certain extent because the limiting plate covers the outer side of the rocker arm link; and the arrangement of the return spring makes it more easy to rotate the rocker arm link downwards, the goggle can be tightly pressed onto the window of the helmet body through part of the elastic force, and the sealing is more reliable.

(3) The arrangement of the air supply system can provide fresh air to the internal portion of the comparatively or completely sealed helmet; and the air supply port is divergent such that the air can be distributed more divergently and uniformly.

(4) The helmet is light, has no change in appearance and is easy to use.

(5) The front protection lens is wide and large enough to ensure a wide field of view.

(6) When in use, the distance to the eyes is relatively short, the sight is better and the comfort in use is improved.

In the drawings, helmet body 1, goggle 2, front protection lens 3, link mechanism 4, link rack 41, sliding groove 411, oval-shaped sliding path 4111, circular hole 412, rocker arm link 42, handle 421, fastener 4211, second hollow cylinder 422, sleeve 423, return spring 424, sliding sleeve 43, protrusion 431, first connecting shaft 5, second connecting shaft 6, third connecting shaft 7, first split body 71, second split body 72, limiting plate 8, sector-shaped groove 81, clamping groove 82, first hollow cylinder 83, notch 84, first sealing plate 85, connecting hole 851, second sealing plate 86, air supply system 9, air supply pipe 91, air supply port 92.

DETAILED DESCRIPTION

The following is a detailed description of the embodiments of the present invention, which are implemented based on the technical solution of the present invention. Detailed implementation and specific operating processes are given, but the scope of protection of the present invention is not limited to the following embodiments.

Embodiment 1

Figure 1:
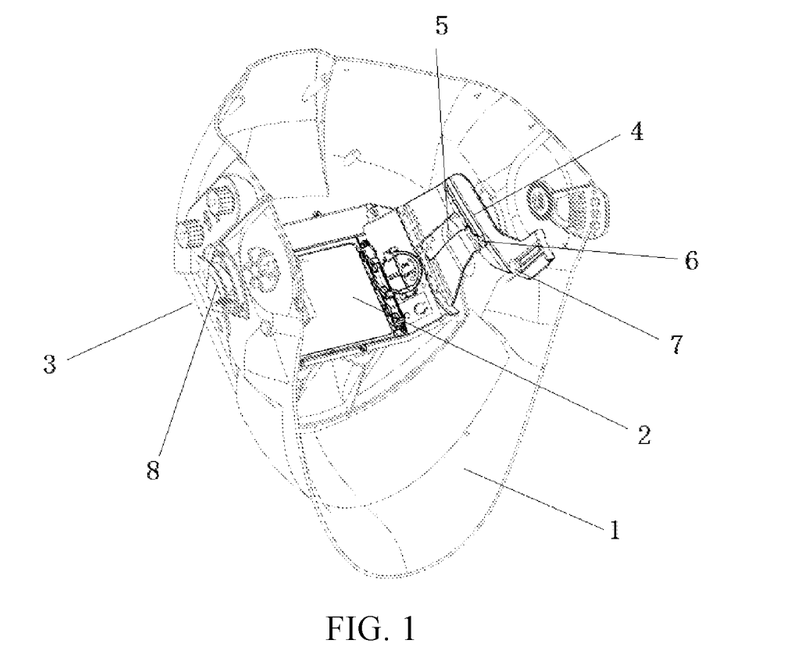
FIG. 1 is a structural schematic view of a helmet with an inwards flipping type goggle according to Embodiment 1 of the present invention.
Figure 2:
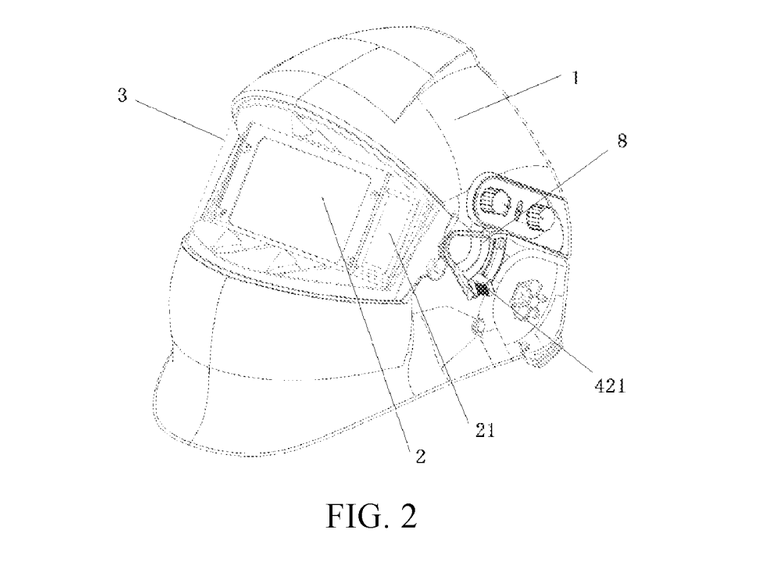
FIG. 2 is a structural schematic view of a helmet with an inwards flipping type goggle according to Embodiment 1 of the present invention.
Figure 3:
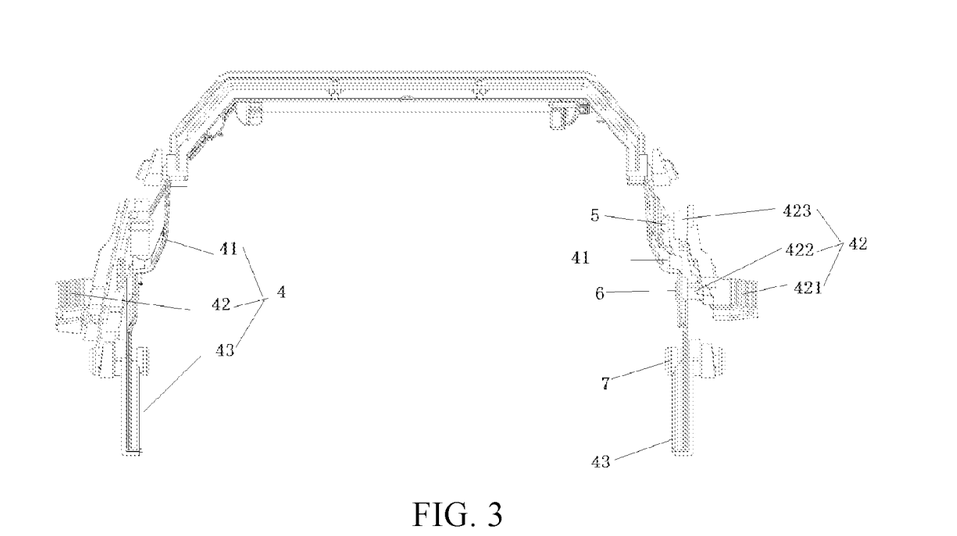
FIG. 3 is a structural schematic view of connection between a connecting mechanism and goggle according to Embodiment 1.

As illustrated in FIG. 1-3, a helmet with an inwards flipping type goggle of this embodiment includes a helmet body 1, a goggle 2, a front protection lens 3 and a link mechanism 4, a first connecting shaft 5, a second connecting shaft 6, a third connecting shaft 7 and a limiting plate 8; the front protection lens 3 is fixed to the front side of the helmet body 1, the goggle 2 is fixed to the link mechanism 4, the link mechanism 4 is capable of adjusting the goggle 2 to be rotatably connected to the two sides of the helmet body 1, the link mechanism 4 is capable of adjusting the goggle 2 to rotate upwards, the goggle 2 is located in the helmet body 1 and at the rear side of the front protection lens 3 and is closer to the eyes; the first connecting shaft 5 and the third connecting shaft 7 are in a fixed state, the second connecting shaft 6 is in a state of being capable of making an arc motion, and the positions of the first connecting shaft 5, the second connecting shaft 6 and the third connecting shaft 7 are sequentially far away from the goggle 2.

Figure 16:
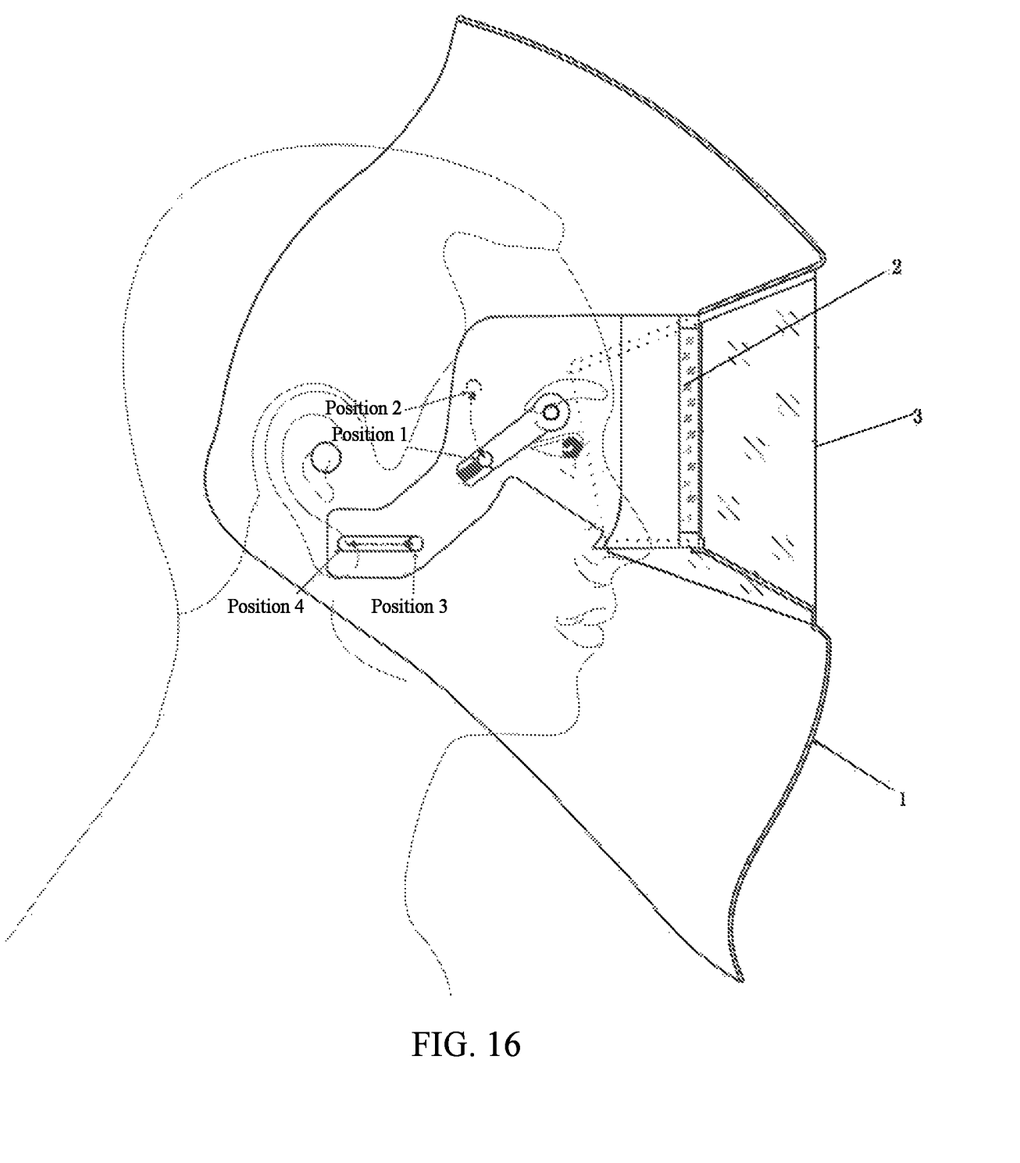
FIG. 16 is a working diagram of goggle in a use state.
Figure 17:
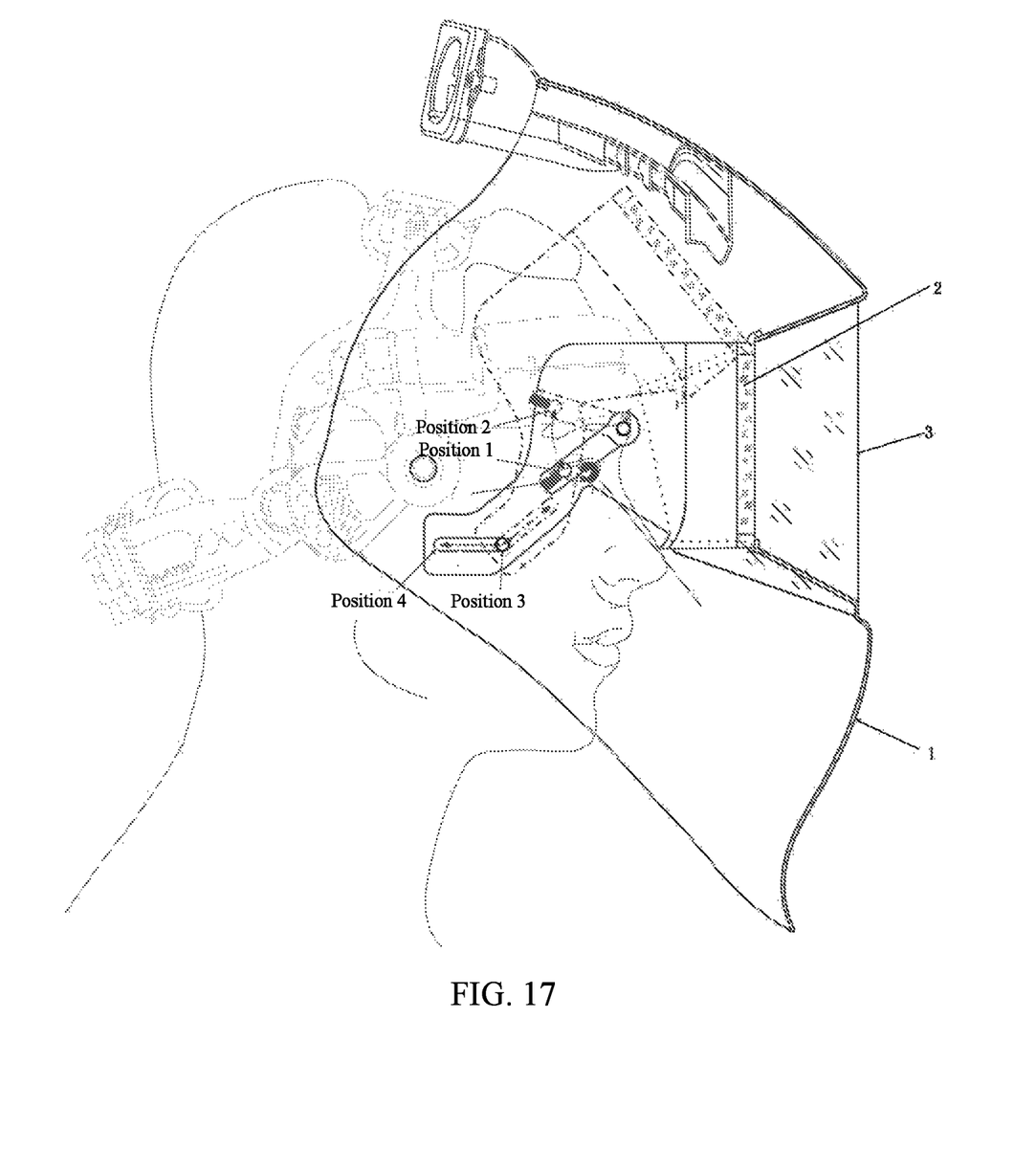
FIG. 17 is a schematic view of goggle at a working position and an upwards flipped position (dashed line).

In this embodiment, referring to working diagrams illustrated in FIG. 16 and FIG. 17, the goggle 2 is arranged in the helmet body 1. When in use, the goggle 2 is closer to the eyes, the sight is better, and the comfort in use is improved. When not in use, the goggle 2 is rotated to the upper side, the outer structure of the helmet body 1 remains unchanged, and the gravity center of the entire helmet will not move forward; and the goggle 2 is always in the helmet no matter at the working position and the upwards flipping position, so as to prevent the goggle from being contaminated and damaged by welding splash, grinding splash and dust. In addition, the front protection lens 3 is wide and large enough to ensure a large field of view.

The goggle in this embodiment may be a fixed-color-number (i.e., fixed transmittance) goggle, an automatic light filtering type variable-color-number (i.e., variable transmittance) goggle, or other lenses suitable for application occasions such as a magnifier.

Figure 12:
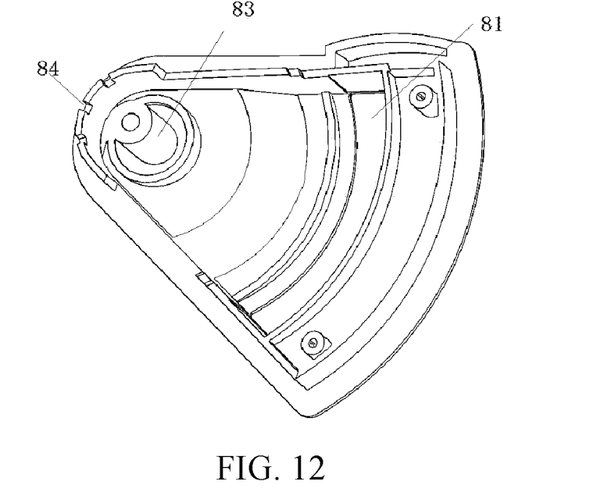
FIG. 12 is a structural schematic view of a limiting plate in Embodiment 1.

As illustrated in FIG. 1-3, in conjunction with FIG. 12, in this embodiment, the helmet body 1 is of a semi-enclosed structure and may be obtained by improving the helmet body 1 designed according to the current specifications, the front side of the helmet body 1 is provided with an opening for mounting the front protection lens 3 and a window closely fit with the goggle 2, the two sides of the helmet body 1 are provided with sector-shaped holes corresponding to the limiting plate 8, the limiting plate 8 is fixed to the sector-shaped holes by means of clamping, screw connection, bonding or the like, the sealing performance at the connecting position is guaranteed, and the rocker arm link 42 sleeves a first hollow cylinder 83 of the limiting plate 8 through a sleeve 423 and is fixed through the first connecting shaft 5, such that one end of the rocker arm link 42 is fixed to the helmet body 1 and the other end can make a rotating motion. In order to optimize the use, the rear side of the helmet body 1 is further provided with a rear protection cover, the rear protection cover is mostly a sealed cover fabric, and the rear protection cover and the helmet body 1 form a cavity capable of accommodating a head. The helmet body 1 is also provided with a plurality of knobs, whose functions are to adjust the color number and sensitivity of the goggle, etc., or some knobs are used to adjust the tightness of the headband, etc., which are all technical solutions that can be realized in the prior art. Therefore, in the present embodiment, there is no significant change in the shape of the helmet, and there is no outwards flipping or outwards protruding type goggle, such that the helmet is more portable and attractive.

Figure 4:
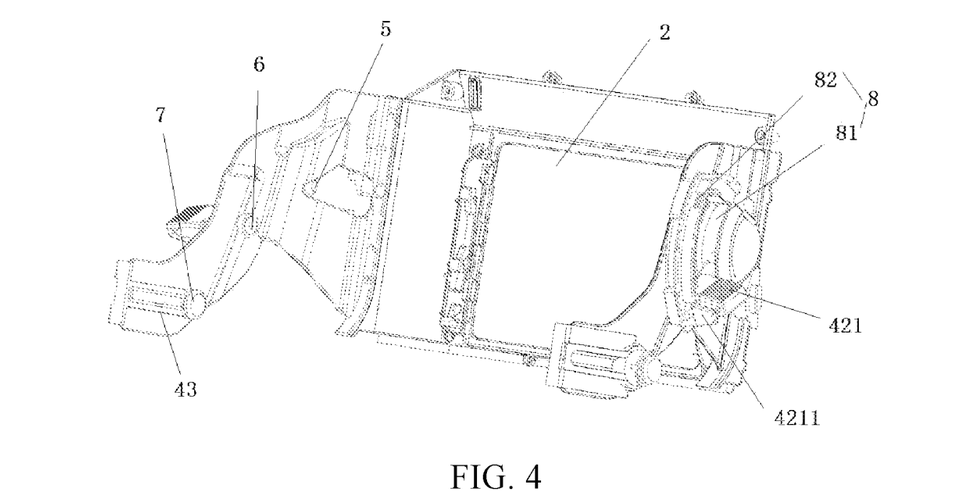
FIG. 4 is a structural schematic view of connection between a connecting mechanism and goggle according to Embodiment 1.
Figure 5:
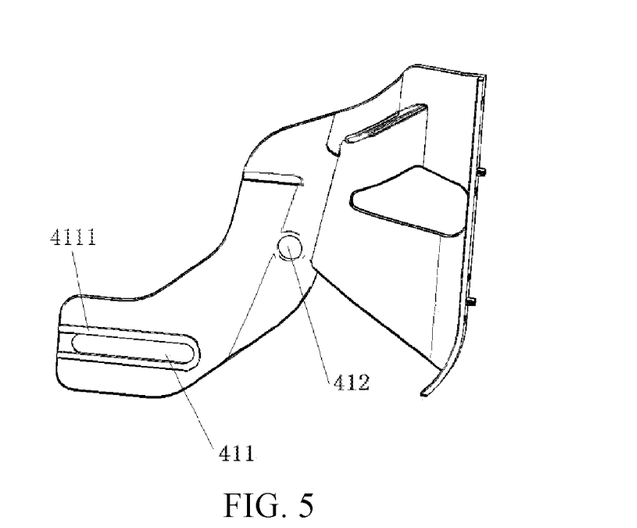
FIG. 5 is a structural schematic view of a link rack in Embodiment 1.

As illustrated in FIG. 3, in conjunction with FIG. 4 and FIG. 5, the right side of FIG. 3 is the structure in which the limiting plate 8 and the fastener 4211 are hidden, so as to facilitate comparison. The link mechanism 4 includes a link rack 41 and a rocker arm link 42, one end of the rocker arm link 42 is rotatably connected to the external portion of the helmet body 1 through the first connecting shaft 5, the rocker arm link 42 is capable of rotating around the first connecting shaft 5 in a certain range, the other end of the rocker arm link 42 is fixedly connected to the middle portion of the link rack 41 through the second connecting shaft 6, the link rack 41 is placed in the helmet body 1, and the link rack 41 is driven to move in the horizontal direction and the vertical direction through the rotation of the rocker arm link 42, one end of the link rack 41 is fixedly connected to the goggle 2, and the other end is slidably connected to the helmet body 1 through the third connecting shaft 7. The link mechanism 4 can ensure that the goggle 2 is moved upwards and rotated rearwards on the whole while the goggle is rotated and upwards flipped, such that it is prevented from interfering with the head and the helmet body 1.

As illustrated in FIG. 5, in conjunction with FIG. 3-4, the link rack 41 is of an elongated "Z" structure, wherein the tail portion is of a horizontal structure, the middle portion is provided with a circular hole 412 for connecting with the rocker arm link 42, the front end of the link rack 41 is of a vertically bent edge structure which is provided with a plurality of connecting holes for connecting with the goggle 2, and the goggle 2 can be connected to the link rack 41 through screws in a replaceable manner, so as to facilitate replacement after parts are damaged. The tail end of the link rack 41 is provided with a horizontal sliding groove 411, the sliding groove 411 is an oval-shaped hole. The third connecting shaft 7 penetrates through the sliding groove 411 and then is fixed to the helmet body 1, the sliding groove 411 can horizontally slide upwards under the limiting function of the third connecting shaft 7.

Figure 6:
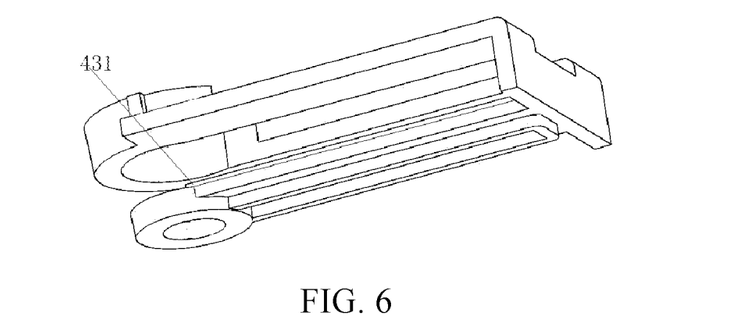
FIG. 6 is a structural schematic view of a sliding sleeve in Embodiment 1.

As illustrated in FIG. 4-6, the sliding groove 411 is further sleeved with a sleeve 43. The sliding sleeve is of a U-shaped structure. The tail portion of the link rack 41 is slidably inserted into the "U-shaped structure". The open end of the U-shaped structure is communicated with the portion, through which the third connecting shaft 7 penetrates, of the link rack 41. In addition, in conjunction with the FIG. 5, the side (inner side surface), facing to the helmet body 1, of the sliding groove 411 is provided with a protruding oval-shaped sliding path 4111, the tail end of the oval-shaped sliding path 411 is open and is used for insertion of a protrusion 431, the lower half of the sliding sleeve 43 illustrated in FIG. 6 is provided with a protrusion 431, and the width of the protrusion 431 is smaller than the width of the oval-shaped sliding path 4111. Thus, the protrusion 431 can be clamped into the oval-shaped sliding path 4111, and the protrusion 431 can slide in the oval-shaped sliding path 4111. The upper half of the sliding sleeve 43 is placed on the outer side surface of the link rack 41. The third connecting shaft 7 sequentially penetrates through the helmet body 1, the upper half of the sliding sleeve 43, the sliding groove 411 and the lower half of the sliding sleeve 43 in a direction from the outside of the helmet body 1 to the inside of the helmet body 1. The lower half of the sliding sleeve 43 is a solid plate, which can seal the sliding groove 411, such that the sliding sleeve 43 seals the entire sliding groove 411 when the goggle 2 is at the working position, thus preventing the hairs of the wearer from entering the sliding groove 411, and being twisted inside when the goggle is upwards flipped. Moreover, the sealed sliding groove 411 is more attractive; and the arrangement of the sliding groove 411 is more conducive to the smooth movement of the link rack 41 inside.

Figure 7:
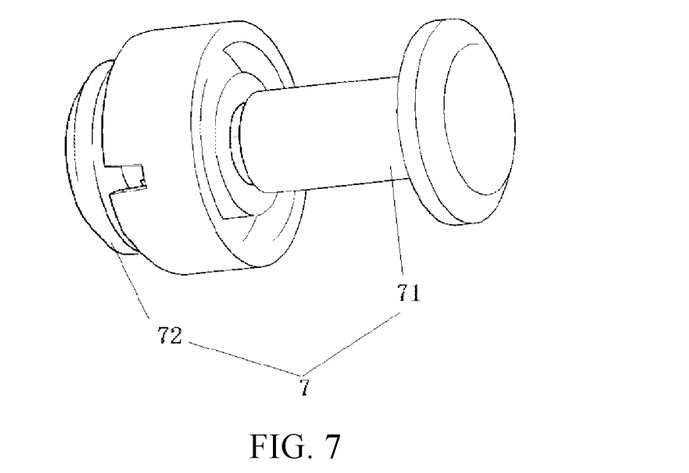
FIG. 7 is a structural schematic view of a third connecting shaft in Embodiment 1.
Figure 8:
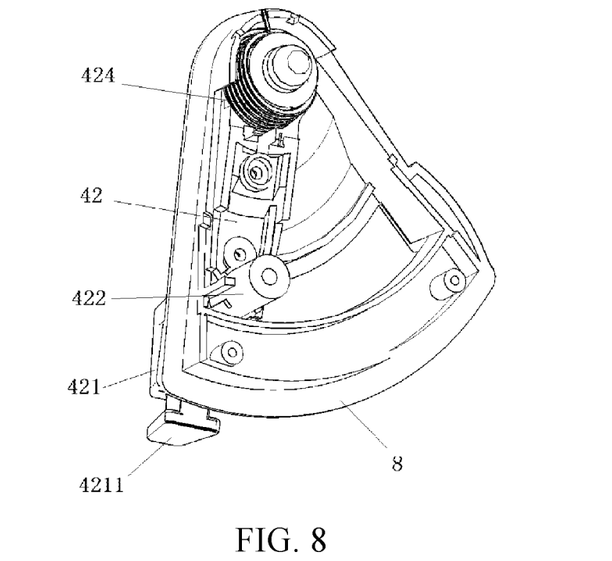
FIG. 8 is a structural schematic view of connection between a rocker arm link and a limiting plate in Embodiment 1.

As illustrated in FIG. 7, the third connecting shaft 7 is of a split structure, including a first split body 71 and a second split body 72. One end of the first split body 71 is of a cylindrical structure with internal threads, and the other end is a protrusion (equivalent to a bolt nut, which plays a role of limiting); the other end of the second split body 72 is of a solid cylindrical structure with external threads which can be fit with the internal threads, and the other end is provided with a protrusion. This embodiment is only a structure of the third connecting shaft 7, and in practical, direct connection by bolts and nuts is also feasible.

Figure 9:
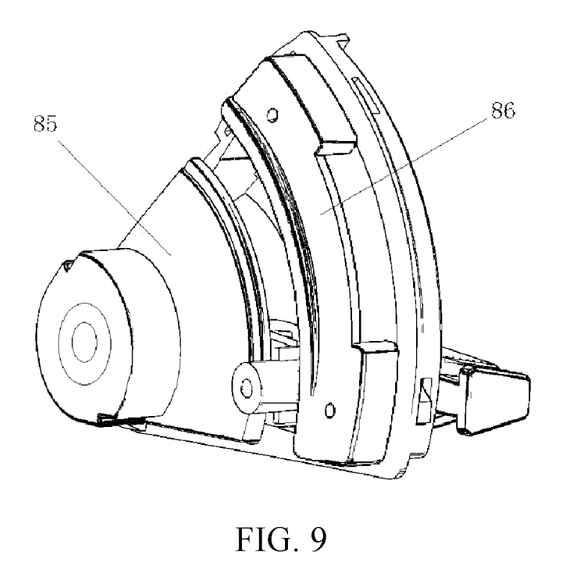
FIG. 9 is a structural schematic view of connection between a first sealing plate and a second sealing plate in Embodiment 1.
Figure 10:
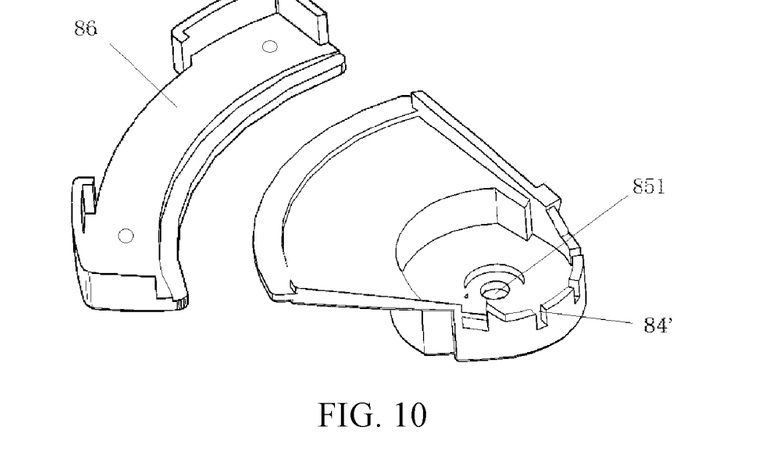
FIG. 10 is a structural schematic view of connection between a first sealing plate and a second sealing plate in Embodiment 1.

As illustrated in FIG. 8-12, in conjunction with FIG. 3, the right portion of FIG. 3 is a structure in which the limiting plate 8 and the fastener 4211 are hidden, so as to facilitate comparison with the left side. In this embodiment, the sector-shaped limiting plate 8 covers the external portion of the rocker arm link 42 and is fixed to the helmet body 1, and the back side of the limiting plate 8 (the side facing to the internal portion of the helmet body 1) is provided with the first hollow cylinder 83 connected to the first connecting shaft 5. The arrangement of the first hollow cylinder 83 is to fit and connect with the first connecting shaft 5 to fix the limiting plate 8 on the helmet body 1, the first connecting shaft 5 is fixed to the hollow internal portion of the first hollow cylinder 83, threaded fixation or interference fit fixation may be adopted, i.e., the first connecting shaft 5 penetrates through the helmet body 1 through the internal portion of the helmet body 1 and then is connected to the first hollow cylinder 83, the connecting position between the rocker arm link 42 and the first hollow cylinder 83 is a sleeve 423, the sleeve 423 sleeves the first hollow cylinder 83 and is not fixed, i.e., the sleeve 423 can rotate on the first hollow cylinder 83. In this embodiment, the rocker arm link 42, the handle 421 and the sleeve 423 are of an integrated structure, the handle 421 penetrates through the sector-shaped groove 81 and extends to the outside of the limiting plate 8, the sleeve 423 is located on the other side of the limiting plate 8 (in FIG. 11, the handle 421 is at the bottom of the left side of the limiting plate, and the sleeve 423 is located at the top of the right side of the limiting plate). A return spring 424 is arranged outside the sleeve 423, one end of the return spring 424 is inserted into the rocker arm link 42, the other end is clamped in the notch 84 of the limiting plate 8, and the notch 84 is located at the edge of the limiting plate 8. In this case, the return spring 424 maintains a certain elastic force. As illustrated in FIG. 9-10, in order to ensure that the return spring 424 does not fall off when it sleeves the sleeve 423 and guarantee the sealing performance and attractiveness, a first sealing plate 85 is further arranged and clamped on the limiting plate 8 and outside the sleeve 423. The first sealing plate 85 is a sector-shaped plate and is fit with the limiting plate 8 in shape, the small end is provided with a connecting hole 851 to allow the first connecting shaft 5 to penetrate through, the position corresponding to the notch 84 is provided with a notch 84', and the return spring 424 is limited in the space formed by the notch 84 and the notch 84'; under the effect of the elastic force, it is more easy to rotate the rocker arm link 42 downwards, the existence of certain elastic force can make the lower edge of the goggle 2 close to the window of the helmet body 1 to ensure the sealing performance. In order to optimize the sealing performance and attractiveness, a second sealing plate 86 may also be arranged on the same side of the first sealing plate 85 and is clamped on the limiting plate 8. The first sealing plate 85 and the second sealing plate 86 are respectively located on two sides of the second hollow cylinder 422, and an arc path is formed between the first sealing plate 85 and the second sealing plate 86.

Figure 11:
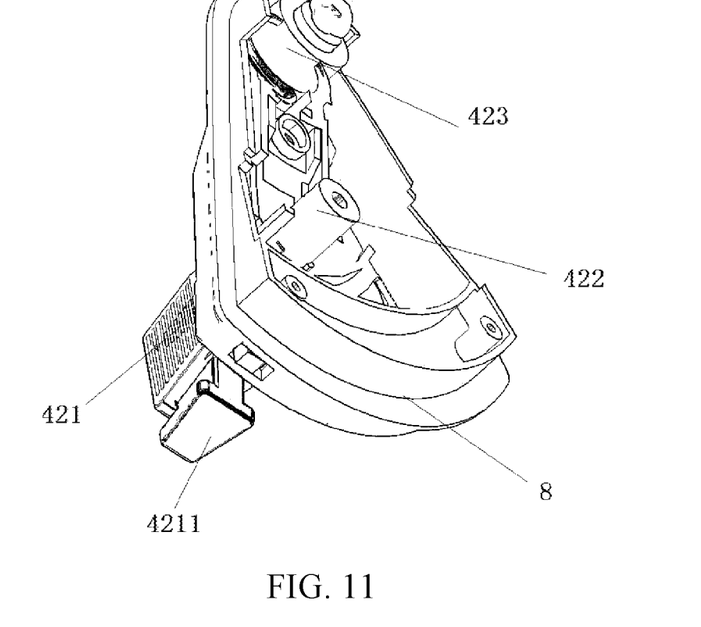
FIG. 11 is a structural schematic view of connection between a rocker arm link and a limiting plate in Embodiment 1.

As illustrated in FIG. 11, a second hollow cylinder 422 is arranged at a position corresponding to the handle 421 on the rocker arm link 42, and the second hollow cylinder 422 and the rocker arm link 42 are of an integrated structure. In conjunction with FIG. 5, the link rack 41 is provided with a circular hole 412 corresponding to the second connecting shaft 6. Correspondingly, the two sides of the helmet body 1 are provided with sector-shaped holes corresponding to the limiting plate 8, and the second hollow cylinder 422 penetrates through the circular hole 412 in the link rack 41 and is in fixed fit connection with the second connecting shaft 6 which penetrates through the internal portion of the helmet body 1 to realize fixed connection between the middle portion of the link rack 41 and the rocker arm link 42.

Figure 13:
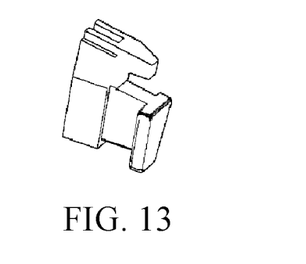
FIG. 13 is a structural schematic view of a fastener in Embodiment 1.

As illustrated in FIG. 12-13, in conjunction with FIG. 3, the large end of the limiting plate 8 is provided with a sector-shaped groove 81; one end, connected to the rocker arm link 42 with the link rack 41, of the rocker arm link 42 is provided with a handle 421, and the handle 421 extends out of the sector-shaped groove 81. The tail portion of the limiting plate 8 is provided with at least two clamping grooves 82. In this embodiment, two clamping grooves 82 are provided. The internal portion of the handle 421 is hollow, a spring mounted in a vertical direction is arranged inside, and the spring is provided with a fastener 4211, as illustrated in FIG. 13, the fastener 4211 is of a concave structure, one end of the concave structure is capable of being clamped in the clamping groove 82, and the other end is on the outer side of the clamping groove 82. In this embodiment, the positioning of goggle 2 at two positions is realized through two clamping grooves 82. Of course, three clamping grooves 82 and so on may also be provided according to the actual needs; and the spring may also be replaced with other elastic pieces such as an elastic sheet.

In conjunction with FIG. 4, when the lower clamping groove 82 and the fastener 4211 on the handle 421 are clamped, the goggle 2 is in a vertical state, i.e., in a use state; when the goggle 2 is not used, the other ends of the fasteners 4211 on the two sides is held by two hands at the same time, the spring is compressed to make the fastener 4211 shrink inwards, the fastener 4211 is no longer clamped in the clamping groove 82, the handle 421 is then operated to rotate along the first connecting shaft 5 and move to the upper clamping groove 82, and then the other end of the fastener 4211 is released. Under the effect of the compression of the spring, the fastener 4211 pops out and is clamped into the upper clamping groove 82 to realize positioning. In this case, the goggle 2 can be fixed at the top of the head, and will not move down.

The operation process in this embodiment is illustrated in FIG. 16-17. When the goggle 2 is located on the front side of the eyes, i.e., in the use state, the rightmost end of the sliding groove 411 is fit with the third connecting shaft 7 (i.e., position 4), and the rocker arm link 42 is located at the lower position (i.e., position 1). When the goggle needs to be moved upwards, as illustrated in FIG. 4, the fasteners 4211 on the two sides are held by two hands at the same time, a compression spring makes the fastener 4211 shrink inwards, the fastener 4211 is no longer clamped in the lower clamping groove 82, then the handle 421 is operated to rotate along the first connecting shaft 5 and move to the upper clamping groove 82, and then the fastener 4211 is released. Under the effect of the spring, the fastener 4211 is clamped into the upper clamping groove 82 to realize positioning. In this case, the rocker arm link 42 is at the upper position (i.e., position 2). Because the rocker arm link 42 moves forwards and upwards, the sliding groove 411 slides upwards horizontally under the effect of the third connecting shaft 7. In this case, the leftmost end of the sliding groove 411 is fit with the third connecting shaft 7 (i.e., position 3), and the goggle 2 is fixed to the front side of the forehead. In the rotation process, the lower edges of the goggle 2 are always in the same vertical plane and are not inclined, such that the goggle can move according to the determined position within the smallest space.

When the goggle needs to be lowered to the working position, the fasteners 4211 on the two sides are held by two hands at the same time, the compression spring makes the fastener 4211 shrink inwards, the fastener 4211 is no longer clamped in the upper clamping groove 82, then the handle 421 is operated to rotate along the first connecting shaft 5 and move to the lower clamping groove 82, and then the fastener 4211 is released. Under the effect of the spring, the fastener 4211 is clamped into the lower sliding groove 82 to realize positioning. In this case, the rightmost end of the sliding groove 411 is fit with the third connecting shaft 7 (i.e., position 4), and the rocker arm link 42 is located at the lower position (i.e., position 1).

Embodiment 2

Figure 14:
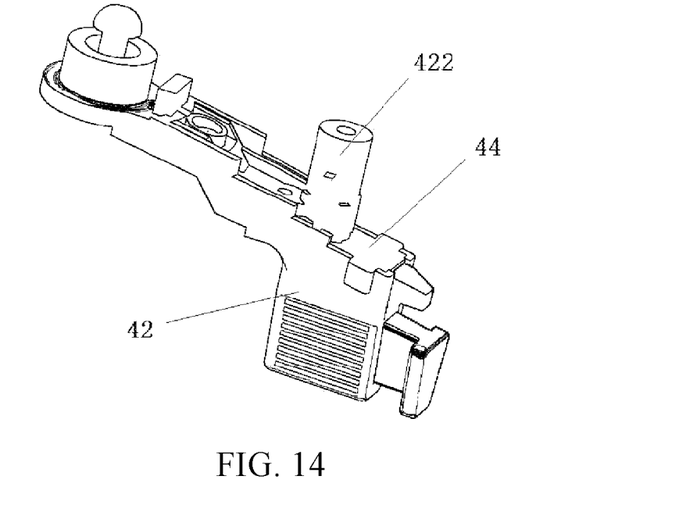
FIG. 14 is a structural schematic view of a rocker arm link and a connecting member in Embodiment 2.

As illustrated in FIG. 14, the difference of Embodiment 2 from Embodiment 1 lies in that the second hollow cylinder 422 is arranged on a connecting member 44, the connecting member 44 and the rocker arm link 42 are of a split structure, and the second hollow cylinder 422 is not directly arranged on the rocker arm link 42.

The rocker arm link 42 and the link rack 41 are connected with each other through a connecting member 44, the connecting member 44 is fixed to the rocker arm link 42, and screw connection, clamping and bonding may be adopted. Specifically, it is connected between the handle 421 and the sleeve 423 to ensure that the middle portion of the link rack 41 is fixedly connected to the end of the rocker arm link 42, a second hollow cylinder 422 fixedly connected to the second connecting shaft 6 is arranged at the position corresponding to the handle 421 on the connecting member 44, and the link rack 41 is provided with a circular hole 412 corresponding to the second connecting shaft 6. Correspondingly, the two sides of the helmet body are provided with sector-shaped holes corresponding to the limiting plate, the sector-shaped holes are designed to adapt to the space when the second connecting shaft 6 makes an arc motion, the second hollow cylinder 422 penetrates through the circular hole in the link rack 41 and is in fixed fit connection with the second connecting shaft 6 penetrating through the internal potion of the helmet body 1 to realize the fixed connection between the middle portion of the link rack 41 and the rocker arm link 42, and other ways such as screw fixed connection or interference fit connection that are capable of realizing fixed connection may be adopted. In this embodiment, the purpose of providing the connecting member 44 is to facilitate the production process of the rocker arm link 42, the fastener 4211 and the second hollow cylinder 422, and the mounting with the limiting plate 8 and the compression spring.

Embodiment 3

The difference of Embodiment 3 from Embodiment 1 lies in that the way for positioning of the rocker arm link 42 is different. In Embodiment 1, the positioning is realized through the fastener 4211 and two clamping grooves 82. In this embodiment, the positioning is realized by inserting a positioning pin into the clamping groove 82.

The tail portion of the limiting plate 8 is provided with at least two clamping grooves 82. In this embodiment, two clamping grooves 82 are provided. The internal portion of the handle 421 is hollow. When the handle 421 moves to one clamping groove 82, the hollow portion of the handle is aligned with the clamping groove 82. In this case, the positioning pin is inserted into the clamping groove 82 and extends to the hollow portion in the handle 421 to realize positioning; and when the position needs to be changed, the positioning pin is pulled out and the handle 421 is moved to another clamping groove 82, the positioning pin is inserted into the clamping groove 82 and extends to the hollow portion in the handle 421 to realize the positioning at other positions.

Embodiment 4

Figure 15:
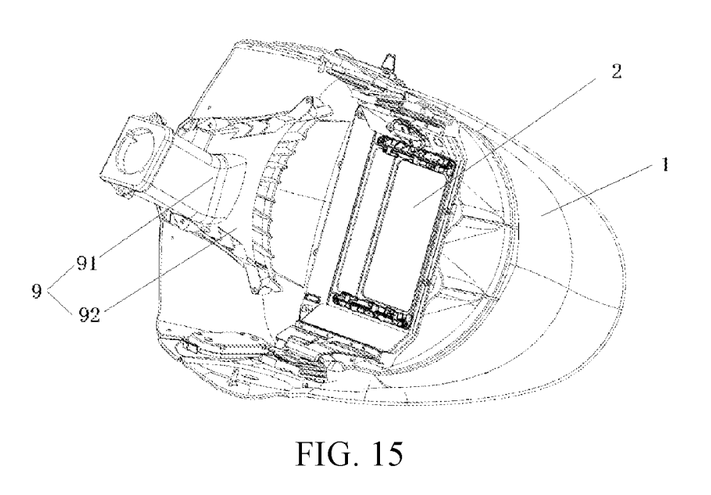
FIG. 15 is a structural schematic view of a helmet with inwards flipping goggle according to Embodiment 4.

As illustrated in FIG. 15, the difference from Embodiment 1 lies in that the helmet body 1 further includes an air supply system 9 on the basis of Embodiment 1.

The air supply system 9 in this embodiment includes an air supply pipe 91 and a an air supply port 92, the air supply port 92 is fixed to the inner side surface of the top of the helmet body, and the air supply pipe 91 is connected to the air supply port 92. The air supply port 92 is of a divergent structure, the air supply port 92 includes a plurality of sub-air supply ports, and the sub-air supply ports can supply air to the front and the two sides of the head to avoid the situation that the operator feel uncomfortable because the air is supply towards one direction.

As an optimized structure, the helmets in Embodiment 1, Embodiment 2, Embodiment 3 and Embodiment 4 are all symmetrical, wherein two link mechanisms 3, two first connecting shafts 5, two second connecting shafts 6, two third connecting shafts 7 and two limiting plates 8 are provided and arranged on the sides of the helmet body 1.

The two sides of the goggle 2 are further provided with solar power supply panels. The solar power supply panels play a role of supplying power to the variable-light goggle by using sunlight and welding light, and adjusting the color number and sensitivity of the goggle 2 through the knob on the helmet body 1.

Embodiment 5

The difference from Embodiment 1 lies in that the rotation of the rocker arm link 42 can be driven by a micro-motor, which can realize the electric control of the upward and downward movement and rotation of the goggle 2, facilitating the operation, effort saving and automation.

The above are only preferred embodiments of the present invention, and are not intended to limit the present invention. Any modification, equivalent replacement and improvement made within the spirit and rule of the present invention shall be included in the scope of protection of the present invention.

What is claimed is:

1. A helmet with an inwards flipping type goggle, comprising a helmet body, a goggle, a front protection lens and a link mechanism; the front protection lens is fixed to a front side of the helmet body, the goggle is fixed to the link mechanism, the link mechanism is capable of adjusting the goggle to move up and down and to be rotatably connected to two sides of the helmet body, and the goggle is located in the helmet body;

the link mechanism comprises a link rack and a rocker arm link, wherein one end of the rocker arm link is rotatably connected to the side surface of the helmet body through a first connecting shaft, another end of the rocker arm link is fixedly connected to a middle portion of the link rack through a second connecting shaft, the link rack is placed in the helmet body, one end of the link rack is fixedly connected to the goggle, the other end is slidably connected to the helmet body through a third connecting shaft, and the first connecting shaft, the second connecting shaft and the third connecting shaft are sequentially far away from the front side of the helmet body, with the first connecting shaft being the closest to the front side of the helmet body and the third connecting shaft being the furthest from the front side of the helmet body;

the helmet further comprising a sector-shaped limiting plate, the limiting plate is fixed to the helmet body and covers an external portion of the rocker arm link, and one end, far from the first connecting shaft, of the limiting plate is provided with a sector-shaped groove; one side, facing to an internal portion of the helmet body, of the limiting plate is provided with a first hollow cylinder, the first hollow cylinder is provided at a small end of the limiting plate, one end of the rocker arm link is provided with a sleeve, the sleeve rotatably sleeves the first hollow cylinder, and the first connecting shaft is in connection with the first hollow cylinder.

2. The helmet with an inwards flipping type goggle according to claim 1, further comprising a return spring, the return spring sleeves the outside of the sleeve, two ends of the return spring are bent, a bottom end is inserted into the rocker arm link and a top end is fixed to the limiting plate.

3. The helmet with an inwards flipping type goggle according to claim 1, wherein one end, connected to the link rack, of the rocker arm link is provided with a handle, the handle is arranged on one side, back on to the helmet body, of the rocker arm link, penetrates through the sector-shaped groove and extends to an outside of the limiting plate, a top end of the handle is provided with a fastener, the fastener is of a concave structure, one end, far away from the first connecting shaft, of the limiting plate is provided with at least two clamping grooves, one end of the fastener is clamped in one of the clamping grooves, another end is clamped outside the clamping grooves, one end, facing to the internal portion of the helmet body, of the rocker arm link is provided with a second hollow cylinder, and the second connecting shaft is in connection with the second hollow cylinder.

4. The helmet with an inwards flipping type goggle according to claim 1, wherein the helmet body is of a semi-enclosed structure, the front side of the helmet body is provided with an opening for mounting the front protection lens and a window compatible with the goggle, the two sides of the helmet body are provided with sector-shaped holes corresponding to the limiting plate, and the limiting plate is fixedly connected at the sector-shaped holes.

* * * * *